(12) United States Patent
Li et al.

(10) Patent No.: US 9,409,932 B2
(45) Date of Patent: Aug. 9, 2016

(54) SILICONE-COMPATIBLE PHOTOINITIATORS

(71) Applicants: Henkel AG & Co. KGAA, Duesseldorf (DE); Henkel IP & Holding GMBH, Duesseldorf (DE)

(72) Inventors: Zhiming Pasing Li, Shanghai (CN); Yong Zhang, Shanghai (CN); Jinyou Li, Shanghai (CN); Zhixiang Lu, Rocky Hill, CT (US); Zheng Lu, South Glastonbury, CT (US)

(73) Assignees: Henkel IP & Holding GmbH, Duesseldorf (DE); Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/729,229

(22) Filed: Jun. 3, 2015

(65) Prior Publication Data

US 2015/0266907 A1 Sep. 24, 2015

Related U.S. Application Data

(63) Continuation of application No. PCT/CN2012/085935, filed on Dec. 5, 2012.

(51) Int. Cl.
*C08F 2/50* (2006.01)
*C08F 2/46* (2006.01)
*C08G 61/04* (2006.01)
(Continued)

(52) U.S. Cl.
CPC ............ *C07F 7/1852* (2013.01); *C07F 5/02* (2013.01); *C07F 7/025* (2013.01); *C07F 7/0849* (2013.01); *C08G 77/14* (2013.01); *C08G 77/80* (2013.01);
(Continued)

(58) Field of Classification Search
CPC ............ C07F 7/1852; C07F 7/05; C07F 5/02; C07F 7/0849; C08G 77/14; C08G 77/80; C08J 2343/04; C08J 3/28; C08K 5/5419
USPC ............ 522/42, 33, 6, 71, 189, 184, 1; 520/1
See application file for complete search history.

(56) References Cited

U.S. PATENT DOCUMENTS 4,273,907 A 6/1981 Takamizawa et al.
4,391,963 A 7/1983 Shirahata
(Continued)

FOREIGN PATENT DOCUMENTS

EP 1072326 A2 1/2001
JP 2008-255062 * 10/2008
(Continued)

OTHER PUBLICATIONS

Creary et al, Diels-Alder Approach to Bicyclic alpha-hydroxy ketones. Facile Ketol Rearrangements of Strained alpha-hydroxy ketones, 1985, 50, 1932-1938.*
(Continued)

*Primary Examiner* — Ling Choi
*Assistant Examiner* — Jessica E Whiteley
(74) *Attorney, Agent, or Firm* — Steven C. Bauman

(57) ABSTRACT

Compounds useful as a photoinitiator and/or photosensitizer represented by the following formula (I):

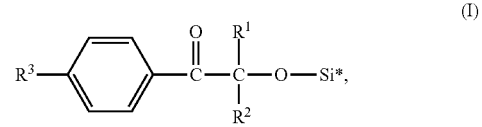

wherein
$R^1$ and $R^2$ each independently designates an alkyl group of 1 to 12 carbon atoms or a cycloalkyl group of 5 or 6 carbon atoms or $R^1$ and $R^2$ form together with the carbon atom to which they are attached a cycloaliphatic ring of 5 or 6 carbon atoms,
Si* represents an organopolysiloxane residue bonded via a silicon atom of this residue to the oxygen shown in formula (I), or a silane group $SiR^4R^5R^6$, wherein $R^4$, $R^5$ and $R^6$ each independently designates an alkyl group of 1 to 12 carbon atoms, a cycloalkyl group of 5 or 6 carbon atoms or an aryl group of 6 to 10 carbon atoms, and
$R^3$ designates a hydrogen atom or a group represented by the following formula (II)

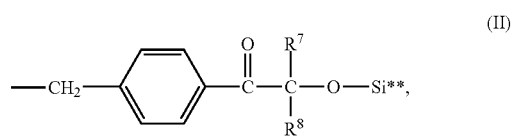

wherein
$R^7$ and $R^8$ each independently designates an alkyl group of 1 to 12 carbon atoms or a cycloalkyl group of 5 or 6 carbon atoms or $R^7$ and $R^8$ form together with the carbon atom to which they are attached a cycloaliphatic ring of 5 or 6 carbon atoms, and
Si** represents an organopolysiloxane residue bonded via a silicon atom of this residue to the oxygen shown in formula (II), or a silane group $SiR^9R^{10}R^{11}$, wherein $R^9$, $R^{10}$ and $R^{11}$ each independently designates an alkyl group of 1 to 12 carbon atoms, a cycloalkyl group of 5 or 6 carbon atoms or an aryl group of 6 to 10 carbon atoms.

17 Claims, No Drawings

(51) Int. Cl.
- C07F 7/18 (2006.01)
- C08G 77/14 (2006.01)
- C08G 77/00 (2006.01)
- C07F 5/02 (2006.01)
- C07F 7/08 (2006.01)
- C08K 5/5419 (2006.01)
- C07F 7/02 (2006.01)
- C08J 3/28 (2006.01)

(52) U.S. Cl.
CPC ............... C08J 3/28 (2013.01); C08K 5/5419 (2013.01); *C08J 2343/04* (2013.01)

(56) References Cited

U.S. PATENT DOCUMENTS

| | | | |
|---|---|---|---|
| 4,536,265 A | | 8/1985 | Fabrizio et al. |
| 4,560,709 A | * | 12/1985 | Berner .................. C08G 59/68 522/100 |
| 5,776,658 A | | 7/1998 | Niesert et al. |
| 6,693,141 B2 | | 2/2004 | Baudin et al. |
| 2005/0239971 A1 | * | 10/2005 | Husler .................. C07C 45/46 525/293 |

FOREIGN PATENT DOCUMENTS

| | | | |
|---|---|---|---|
| WO | 2004-009651 | * | 1/2004 |
| WO | 2004009651 A1 | | 1/2004 |

OTHER PUBLICATIONS

Hunig et al, Einflub der Umpolungsgruppe auf die Diastereoselektivitat der nucleophilen Acylierung alph-chiraler Carbonylverbindungen, 1989, Chem. Ber., 122, 1329-1339.*

Olah et al, Trifluoromethanesulfonic (Triflic) Acid Catalyzed Transformations of alpha-hydroxy carbonyl compounds, 1991, J. Orgl. Chem., 56, 2531-2534.*

Hojo et al, Magnanese Ate Complexes as New Reducing Agetns: Perfectly Regiocontrolled Generation and REactions of the Manganese Enolates with Electrophiles, 1997, J. Am. Chem. Soc., 119, 5459-5460.*

Blackwell et al, B(C6F5)3-Catalyzed Silation of Alcohols: A mild, General Method for Synthesis of Silyl Ethers, Jun. 9, 1999, J. Org. Chem., 64, 4887-4892.*

Shindo et al, Heteroatom-Guided Torquoselective Olefination of alpha-oxy and alpha-amino ketones via Ynolates, Sep. 28, 2005, Chem. Eur., 12, 524-536.*

Robertson et al, Preparation of silyl enol ethers from acyloin derivatives using silyllithium reagents, Feb. 6, 2008, Tetrahedron Letters, 49, 2088-2090.*

Honma et al, JP 2008-255062 Machine Translation, Oct. 23, 2008.*

Tarr et al, Lanthanum Tricyanide-Catalyzed Acyl Silane-Ketone Benzoin Additions and Kinetic Resolution of Resultant alpha-silyloxyketones, Apr. 14, 2010, J. Org. Chem., 75, 3317-3325.*

Mitsuru Shindo et al., Heteroatom-Guided Torquoselective Olefination of α-Oxy and α-Amino Ketones via Ynolates, Chemistry—A European Journal, 2006, vol. 12, No. 2, pp. 524-536.

George A. Olah et al., Trifluoromethanesulfonic (Triflic) Acid Catalyzed Transformations of α-Hydroxy Carbonyl Compounds, J. Org. Chem., 1991, vol. 56, No. 7, pp. 2531-2534.

Siegfried Huenig et al., Trimethylsilyl Cyanide—A Reagent for Umpolung, XVI. Effect of Umpolung Moieties on the Diastereoselectivity of the Nucleophilic Acylation of α-Chiral Carbonyl Compounds, Chemische Berichte, 1989, vol. 122, No. 7, pp. 1329-1339.

Xavier Creary et al., Diels-Alder Approach to Bicyclic α-Hydroxy Ketones. Facile Ketol Reaarrangements of Strained α-Hydroxy Ketones. J. Org. Chem., 1985, vol. 50, No. 11, pp. 1932-1938.

James M. Blackwell et al., B(C6F5)3-Catalyzed Silation of Alcohols: A Mild, General Method for Synthesis of Silyl Ethers, J Org. Chem. 1999, vol. 64, No. 13, pp. 4887-4892.

International Search Report for International Application No. PCT/CN2012/085935 dated Sep. 19, 2013.

George A. Olah et al., Trifluoromethanesulfonic (Triflic) acid catalyzed transformations of a-hydroxy carbonyl compounds. J. Org. Chem., 1991, vol. 56, No. 7, pp. 2531-2534.

Huenig Siegfried et al., Trimethylsilyl cyanide—a reagent for umpolung, XVI. Effect of umpolung moieties on the diastereoselectivty of the nucleophilic acylation of a-chiral carbonyl compounds, Chemische Berichte, 1989, vol. 122, No. 7, pp. 1329-1339.

Xavier Creary et al., Diels-Alder approach to bicyclic a-hydroxy ketones, facile ketol reaarrangements of strained a-hydroxy ketones. J. Org. Chem., 1985, vol. 50, No. 11, pp. 1932-1938.

James M. Blackwell et al., B(C6F5)3-catalyzed silation of alcohols: a mild, general method for synthesis of silyl ethers, J org. Chemc. 1999, vol. 64, No. 13, pp. 4887-4892.

Mitsuru Shindo et al., Geteroatom-guided torquoselective olefination of a-oxy and a-amino ketons via ynolates, Chemistry—A European Journal, 2006, vol. 12, No. 2, pp. 524-536.

* cited by examiner

SILICONE-COMPATIBLE PHOTOINITIATORS

FIELD OF THE INVENTION

The present invention relates to novel silicone-compatible photoinitiators based on an α-hydroxy ketone moiety chemically bonded to an organopolysiloxane (silicone) or a silane, the production thereof by dehydrogenation, as well as their use. The photoinitiators are soluble in silicones and, hence, particularly useful to initiate photocuring of compositions comprising silicones having unsaturated free-radical curable functional groups. Due to their remarkable stability the photoinitiators do not give rise to yellowing and may be used for example in the preparation of optically clear silicone sealants and coatings.

BACKGROUND ART

The photoinduced polymerization of monomers or oligomers comprising functional groups prone to radical reactions is a widely used technique in the production of polymers. To start the reaction usually photoinitiators are added to the monomers or oligomers and the mixture is then exposed to electromagnetic radiation. Many photoinitiators are available which are readily soluble in unsaturated organic resins, and effectively cure these. However, many of these photoinitiators have poor solubility, and therefore unsatisfactory curing effectiveness, in silicones. Such photoinitiators separate from the silicone matrix during storage causing severe haze in any cured product produced. This is not acceptable if the products are intended to be used for optical clear display applications. In order to increase solubility in and hence compatibility with silicones it has been proposed to chemically bond the photoinitiators to organopolysiloxanes or silanes.

U.S. Pat. No. 4,273,907 discloses a novel class of organopolysiloxane compounds comprising at least one benzoin group chemically bonded to a silicon atom of the organopolysiloxane molecule. Such compounds may be prepared by the dehydrohalogenation, dehydrogenation, dehydration or dealkoholation condensation reaction between a corresponding organopolysiloxane having silicon-bonded halogen atoms, hydrogen atoms, hydroxyl groups or alkoxy groups and a benzoin compound in the presence of a suitable reaction promoter or a condensation catalyst. They are soluble in silicone compositions and useful as a photosensitizer in photocurable organopolysiloxane compositions. However, the compounds do not show sufficient stability and tend to cause yellowing upon exposure to heat and/or UV radiation over a longer period. Hence, they are not suitable to be used in high-performance transparent coatings, encapsulants or sealants.

U.S. Pat. No. 4,391,963 also discloses novel photosensitizers, being organopolysiloxane compounds bearing at least one chemically bonded benzoin group. Here, however, the compounds are prepared by hydrosilylation of an alkenyl-substituted benzoin and a silicon compound containing at least one silicon-bonded hydrogen atom. Hence, the organopolysiloxane moiety and the benzoin group are bonded via a divalent hydrocarbon group. This results in an increased stability against hydrolysis, however, requires a comparatively elaborate preparation process since alkenyl-substituted benzoins are not readily available, but have to be synthesized in a separate reaction step.

From U.S. Pat. No. 4,536,265 are known further organopolysiloxane photoinitiators. At least one siloxane unit per molecule comprises an acetophenone photomoiety bonded to the silicon atom of the siloxane unit via a divalent hydrocarbon group having between 2 and 10 carbon atoms. Such a binding group shows high stability against hydrolysis. However, again alkenyl-substituted acetophenones are not readily available, but have to be synthesized in a separate reaction step, making the overall process to produce the organopolysiloxane photoinitiators complex. Moreover, acetophenone moieties tend to cause yellowing upon exposure to heat and/or UV radiation over a longer period.

U.S. Pat. No. 5,776,658 describes silicone-compatible photoinitiators comprising a silane or organopolysiloxane residue bearing a chemically bonded radical of a compound which has one or more of a photoinitiator or photosensitizer activity and which has at least one carbonyl group located on an aromatic nucleus. Again, the bonding of the silane or organopolysiloxane residue and the photomoiety is effected via a divalent hydrocarbon group. This divalent hydrocarbon group is attached to an aromatic carbon atom which is positioned ortho to the carbonyl group of the photomoiety. The photoinitiators show good stability against hydrolysis. The examples disclose preparation of the photoinitiators via a one-pot reaction. However, the resulting product mixture needs to be concentrated and worked up by chromatography. So the overall process is complex and time-consuming. Moreover, the yields of photoinitiator are rather low, e.g. only 17% in example 5.

EP 1072326 A2 provides siloxane-containing surface-active photoinitiators which concentrate on the surface of the formulation. These photoinitiators are used in a method for producing scratch-resistant coatings from formulations containing ethylenic compounds. The photomoiety comprises an aromatic ring which is linked via a bridging unit Y to a silicon atom of the siloxane residue. Due to the surface-active properties of these photoinitiators they will not be homogeneously distributed throughout the formulation and, hence, are not suitable to be used in high-performance transparent coatings, encapsulants or sealants.

It is evident from the above documents that although many photoinitiators have been developed which may be used in the curing of silicone resins there is still need for improvement.

SUMMARY OF THE INVENTION

The object of the invention is to provide novel silicone-compatible photoinitiators, which are accessible from readily available starting materials via a simple one-step reaction. They shall be highly soluble in photocurable silicones and stable against thermal stress, UV radiation and hydrolysis to avoid yellowing of any cured product comprising such photoinitiator. Such photoinitiators are useful for example in the production of optically clear displays.

The inventors found that specific compounds based on α-hydroxy ketone photomoieties bonded to a silicon atom of an organopolysiloxane or silane via a —O—Si bond show the desired properties.

In a first aspect the invention relates to a compound represented by the following formula (I):

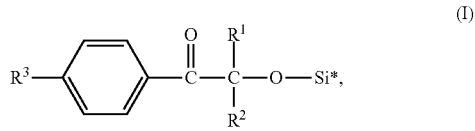

wherein
—$R^1$ and $R^2$ each independently designates an alkyl group of 1 to 12 carbon atoms or a cycloalkyl group of 5 or 6 carbon atoms or $R^1$ and $R^2$ form together with the carbon atom to which they are attached a cycloaliphatic ring of 5 or 6 carbon atoms, —Si* represents an organopolysiloxane residue bonded via a silicon atom of this residue to the oxygen shown in formula (I), or a silane group $SiR^4R^5R^6$, wherein $R^4$, $R^5$ and $R^6$ each independently designates an alkyl group of 1 to 12 carbon atoms, a cycloalkyl group of 5 or 6 carbon atoms or an aryl group of 6 to 10 carbon atoms, and —$R^3$ designates a hydrogen atom or a group represented by the following formula (II)

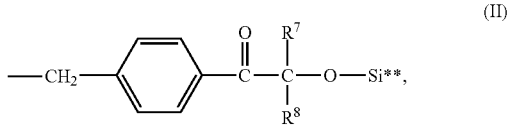

wherein
—$R^7$ and $R^8$ each independently designates an alkyl group of 1 to 12 carbon atoms or a cycloalkyl group of 5 or 6 carbon atoms or $R^7$ and $R^8$ form together with the carbon atom to which they are attached a cycloaliphatic ring of 5 or 6 carbon atoms, and —Si** represents an organopolysiloxane residue bonded via a silicon atom of this residue to the oxygen shown in formula (II), or a silane group $SiR^9R^{10}R^{11}$, wherein $R^9$, $R^{10}$ and $R^{11}$ each independently designates an alkyl group of 1 to 12 carbon atoms, a cycloalkyl group of 5 or 6 carbon atoms or an aryl group of 6 to 10 carbon atoms.

These compounds are readily soluble in photocurable silicones and stable against thermal stress, UV radiation and hydrolysis and, hence, useful photoinitiators to produce cured products based on silicones which do not show yellowing even after a long time.

The present invention furthermore provides a convenient method to produce these compounds by reacting at least one α-hydroxy ketone of formula (I')

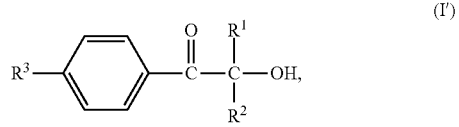

wherein
—$R^1$ and $R^2$ each independently designates an alkyl group of 1 to 12 carbon atoms or a cycloalkyl group of 5 or 6 carbon atoms or $R^1$ and $R^2$ form together with the carbon atom to which they are attached a cycloaliphatic ring of 5 or 6 carbon atoms, and
—$R^3$ designates a hydrogen atom or a group represented by the following formula (II')

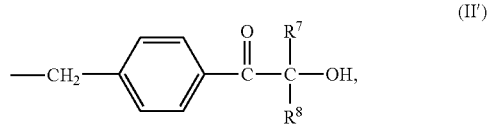

wherein
—$R^7$ and $R^8$ each independently designates an alkyl group of 1 to 12 carbon atoms or a cycloalkyl group of 5 or 6 carbon atoms or $R^7$ and $R^8$ form together with the carbon atom to which they are attached a cycloaliphatic ring of 5 or 6 carbon atoms, and at least one organopolysiloxane having at least one SiH group per molecule or at least one silane $HSiR^4R^5R^6$, wherein $R^4$, $R^5$ and $R^6$ each independently designates an alkyl group of 1 to 12 carbon atoms, a cycloalkyl group of 5 or 6 carbon atoms or an aryl group of 6 to 10 carbon atoms, in the presence of a dehydrogenation catalyst.

Furthermore, the present invention relates to the use of these compounds as photoinitiator and/or photosensitizer, and in particular a method of using these compounds as photoinitiator and/or photosensitizer, comprising addition of the compound to a photopolymerizable organopolysiloxane or silicone resin and exposure of the resulting mixture to electromagnetic radiation.

DETAILED DESCRIPTION

The compounds according to the invention may be used as photoinitiators and/or photosensitizers, being particularly effective if used in compositions based on photocurable silicones.

They show particularly advantageous properties, if both $R^1$ and $R^2$ each independently designates methyl, ethyl, n-propyl or isopropyl, or $R^1$ and $R^2$ form together with the carbon atom to which they are attached a cyclohexyl ring. Such compounds are therefore preferred. Preferably, $R^1$ and $R^2$ each independently designates methyl or ethyl, or $R^1$ and $R^2$ form together with the carbon atom to which they are attached a cyclohexyl ring. Particularly preferred, $R^1$ and $R^2$ both designate methyl, or $R^1$ and $R^2$ form together with the carbon atom to which they are attached a cyclohexyl ring.

In a first preferred embodiment, $R^3$ designates a hydrogen atom.

In a second preferred embodiment $R^3$ designates a group represented by formula (II), wherein $R^7$ and $R^8$ each independently designates methyl, ethyl, n-propyl or isopropyl, or $R^7$ and $R^8$ form together with the carbon atom to which they are attached a cyclohexyl ring. Particularly preferred, $R^7$ and $R^8$ both designate methyl, or $R^7$ and $R^8$ form together with the carbon atom to which they are attached a cyclohexyl ring. In this particular embodiment it is preferred that $R^7$ and $R^8$ are identical to $R^1$ and $R^2$.

Si* in formula (I) represents an organopolysiloxane residue bonded via a silicon atom of this residue to the oxygen shown in formula (I), or a silane group $SiR^4R^5R^6$, wherein $R^4$, $R^5$ and $R^6$ each independently designates an alkyl group of 1 to 12 carbon atoms, a cycloalkyl group of 5 or 6 carbon atoms or an aryl group of 6 to 10 carbon atoms.

If Si* represents a silane group $SiR^4R^5R^6$, it is preferred that $R^4$, $R^5$ and $R^6$ each independently designates an alkyl group of 1 to 10 carbon atoms, preferably selected from methyl, ethyl, n-propyl, isopropyl, n-butyl, isobutyl, tert.-butyl, n-pentyl, isopentyl, 2,2-dimethylpropyl, n-hexyl, isohexyl, 2,2-dimethylbutyl, n-octyl, n-nonyl, and n-decyl, a cycloalkyl group of 5 or 6 carbon atoms, preferably selected from cyclopentyl and cyclohexyl, or an aryl group of 6 to 10 carbon atoms, preferably selected from phenyl and benzyl. It is particularly preferred that $R^4$, $R^5$ and $R^6$ each independently designates an alkyl group selected from methyl, ethyl, n-propyl, isopropyl, n-butyl, isobutyl and tert.-butyl, a cycloalkyl group selected from cyclopentyl and cyclohexyl, or an aryl group selected from phenyl and benzyl. More preferred $R^4$, $R^5$ and $R^6$ each independently designates an alkyl group selected from methyl, ethyl, n-propyl, and isopropyl, a cyclohexyl group, or a phenyl group. Even more preferred $R^4$, $R^5$ and $R^6$ each independently designate methyl, ethyl, n-propyl or isopropyl.

If Si* represents an organopolysiloxane residue this residue is bonded via a silicon atom of this residue to the oxygen shown in formula (I). In other words the organopolysiloxane has at least one siloxane unit $X_a R_b O_{(4-a-b)/2}$, wherein a is an integer of 1 to 3, b is an integer of 0 to 2 and a+b equals 1 to 3; R is a hydrocarbon group of 1 to 10 carbon atoms which may be substituted by one or more halogen atoms; and X is a residue of formula (I")

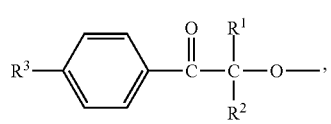

(I")

wherein $R^1$, $R^2$ and $R^3$ each has the meaning and preferred meaning outlined above.

It is preferred that R is an alkyl group of 1 to 10 carbon atoms, preferably selected from methyl, ethyl, n-propyl, isopropyl, n-butyl, isobutyl, tert.-butyl, n-pentyl, isopentyl, 2,2-dimethylpropyl, n-hexyl, isohexyl, 2,2-dimethylbutyl, n-octyl, n-nonyl, and n-decyl, an alkenyl group of 2 to 10 carbon atoms, preferably selected from vinyl, allyl, but-1-enyl, but-2-enyl, and but-3-enyl, a cycloalkyl group of 5 or 6 carbon atoms, preferably selected from cyclopentyl and cyclohexyl, or an aryl group of 6 to 10 carbon atoms, preferably selected from phenyl and benzyl. It is particularly preferred that R designates an alkyl group selected from methyl, ethyl, n-propyl, isopropyl, n-butyl, isobutyl and tert.-butyl, an alkenyl group selected from vinyl, allyl, and but-3-enyl, a cycloalkyl group selected from cyclopentyl and cyclohexyl, or an aryl group selected from phenyl and benzyl. More preferred R designates an alkyl group selected from methyl, ethyl, n-propyl, isopropyl, and tert.-butyl, an alkenyl group selected from vinyl, and allyl, a cyclohexyl group, or a phenyl group. Even more preferred R designate methyl or phenyl. Si** in formula (II) represents an organopolysiloxane residue bonded via a silicon atom of this residue to the oxygen shown in formula (II), or a silane group $SiR^9R^{10}R^{11}$, wherein $R^9$, $R^{10}$ and $R^{11}$ each independently designates an alkyl group of 1 to 12 carbon atoms, a cycloalkyl group of 5 or 6 carbon atoms or an aryl group of 6 to 10 carbon atoms.

If Si** represents a silane group $SiR^9R^{10}R^{11}$, it is preferred that $R^9$, $R^{10}$ and $R^{11}$ each independently designates an alkyl group of 1 to 10 carbon atoms, preferably selected from methyl, ethyl, n-propyl, isopropyl, n-butyl, isobutyl, tert.-butyl, n-pentyl, isopentyl, 2,2-dimethylpropyl, n-hexyl, isohexyl, 2,2-dimethylbutyl, n-octyl, n-nonyl, and n-decyl, a cycloalkyl group of 5 or 6 carbon atoms, preferably selected from cyclopentyl and cyclohexyl, or an aryl group of 6 to 10 carbon atoms, preferably selected from phenyl and benzyl. It is particularly preferred that $R^9$, $R^{10}$ and $R^{11}$ each independently designates an alkyl group selected from methyl, ethyl, n-propyl, isopropyl, n-butyl, isobutyl and tert.-butyl, a cycloalkyl group selected from cyclopentyl and cyclohexyl, or an aryl group selected from phenyl and benzyl. More preferred $R^9$, $R^{10}$ and $R^{11}$ each independently designates an alkyl group selected from methyl, ethyl, n-propyl, and isopropyl, a cyclohexyl group, or a phenyl group. Even more preferred $R^9$, $R^{10}$ and $R^{11}$ each independently designate methyl, ethyl, n-propyl or isopropyl.

If Si** represents an organopolysiloxane residue this residue is bonded via a silicon atom of this residue to the oxygen shown in formula (II). In other words the organopolysiloxane has at least one siloxane unit $X'_{a'}R'_{b'}O_{(4-a'-b')/2}$, wherein a' is an integer of 1 to 3, b' is an integer of 0 to 2 and a'+b' equals 1 to 3; R' is a hydrocarbon group of 1 to 10 carbon atoms which may be substituted by one or more halogen atoms; and X' is a residue of formula (II")

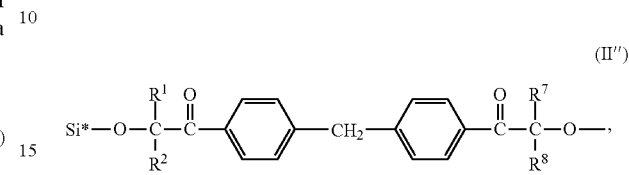

(II")

wherein Si*, $R^1$, $R^2$, $R^7$ and $R^8$ each has the meaning and preferred meaning outlined above.

It is preferred that R' is an alkyl group of 1 to 10 carbon atoms, preferably selected from methyl, ethyl, n-propyl, isopropyl, n-butyl, isobutyl, tert.-butyl, n-pentyl, isopentyl, 2,2-dimethylpropyl, n-hexyl, isohexyl, 2,2-dimethylbutyl, n-octyl, n-nonyl, and n-decyl, an alkenyl group of 2 to 10 carbon atoms, preferably selected from vinyl, allyl, but-1-enyl, but-2-enyl, and but-3-enyl, a cycloalkyl group of 5 or 6 carbon atoms, preferably selected from cyclopentyl and cyclohexyl, or an aryl group of 6 to 10 carbon atoms, preferably selected from phenyl and benzyl. It is particularly preferred that R' designates an alkyl group selected from methyl, ethyl, n-propyl, isopropyl, n-butyl, isobutyl and tert.-butyl, an alkenyl group selected from vinyl, allyl, and but-3-enyl, a cycloalkyl group selected from cyclopentyl and cyclohexyl, or an aryl group selected from phenyl and benzyl. More preferred R' designates an alkyl group selected from methyl, ethyl, n-propyl, isopropyl, and tert.-butyl, an alkenyl group selected from vinyl, and allyl, a cyclohexyl group, or a phenyl group. Even more preferred R' designate methyl or phenyl.

If $R^3$ in formula (I) designates a group represented by formula (II), it is preferred that Si** is identical to Si*. Particularly preferred Si** is identical to Si*, and $R^7$ and $R^8$ are identical to $R^1$ and $R^2$.

Especially preferred according to the invention are the following compounds:
  compound of formula (1), wherein $R^1$ and $R^2$ each designates methyl and $R^3$ designates a hydrogen atom;
  compound of formula (1), wherein $R^1$ and $R^2$ form together with the carbon atom to which they are attached a cyclohexyl ring and $R^3$ designates a hydrogen atom; and
  compound of formula (1), wherein $R^1$ and $R^2$ each designates methyl and $R^3$ designates a group represented by formula (II), wherein $R^7$ and $R^8$ each designates methyl.

Compounds according to the invention are readily available by reacting at least one α-hydroxy ketone of formula (I')

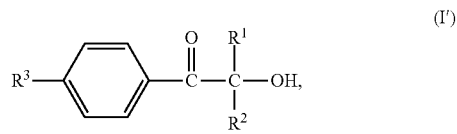

(I')

wherein $R^1$, $R^2$ and $R^3$ have the meaning and preferred meanings as outlined above and at least one organopolysiloxane having at least one SiH group per molecule or at least one silane HSiR$^4$R$^5$R$^6$, wherein R$^4$, R$^5$ and R$^6$ have the meaning and preferred meanings as outlined above, in the presence of a dehydrogenation catalyst.

Preferably, the α-hydroxy ketone of formula (I') and the organopolysiloxane having at least one SiH group per molecule or the silane HSiR$^4$R$^5$R$^6$ are reacted in respective amounts to provide a molar ratio of hydroxyl groups of the α-hydroxy ketone of formula (I') to SiH groups of 0.8 to 1.2, preferably 1.0 to 12.

Preferably, the reaction is carried out at a temperature of from 20 to 100° C., particularly preferred of from 20 to 60° C., more preferred of from 30 to 60° C.

It is preferred to provide a mixture of the α-hydroxy ketone and the dehydrogenation catalyst and to add the organopolysiloxane or silane dropwise under stirring.

Reaction time is preferably from 0.5 to 24 hours, particularly preferred from 0.5 to 5 hours.

There are no particular restrictions with regard to the dehydrogenation catalyst. All known dehydrogenation catalyst may be used. However, the dehydrogenation catalyst is preferably selected from tris(pentafluorobenzene)borane, zinc dust, and platinum catalysts, tris(pentafluorobenzene)borane being particularly preferred.

The obtained photoinitiators are clear and highly soluble in silicone compositions and, hence, can be blended in high amounts into such compositions.

A further object of the invention is the use of these compounds as photoinitiator and/or photosensitizer, in particular a method of using the compound according to the invention as photoinitiator and/or photosensitizer, comprising addition of the compound to a photopolymerizable organopolysiloxane or silicone resin and exposure of the resulting mixture to electromagnetic radiation. Although there is no particular limitation regarding the photopolymerizable organopolysiloxane or silicone resin, it is preferred to add the compound according to the invention to a composition based solely or predominately on (meth)acryloxysiloxanes, since photo curing such mixtures results in products having a degree of haze of less than 1%, and showing very good thermal, hydrolytic, and UV stability. Useful electromagnetic radiation is any radiation which will provoke forming of radicals and, hence, start a free-radical polymerization of the photopolymerizable organopolysiloxane or silicone resin. An example thereof is actinic radiation.

A further object of the invention is a curable composition comprising at least a compound according to the invention and at least one photopolymerizable organopolysiloxane or silicone resin, preferably a (meth)acryloxysiloxane. The amount of the compound according to the invention in such compositions may vary within broad limits. Preferably, the composition comprises the compound according to the invention or a mixture of several compounds according to the invention in a total amount of 0.1 to 30% by weight, preferably 0.2 to 15% by weight, based on the weight of the composition. The remainder generally consists solely or predominantly of photopolymerizable organopolysiloxane or silicone resin.

Below is a description of particular aspects of the present invention using a series of examples, however, the present invention is in no way restricted to the below presented examples.

EXAMPLES

Synthesis Example 1

16.42 g (0.1 mol) Darocur 1173 (CAS 7473-98-5; 2-hydroxy-2-methylpropiophenone available from BASF SE) and 0.12 g tris(pentafluorobenze)borane were added into a 100 ml glass flask and heated to 60° C. 24.37 g (0.11 mol) of bis(trimethylsiloxy)methylsilane was added dropwise under stirring (30 minutes). The resulting mixture was stirred for another 30 minutes and then distilled under reduced pressure to obtain the desired siloxane modified photoinitiator. The obtained siloxane modified photoinitiator was a clear, light yellowish liquid.

The conversion yield of Darocur 1173 was 98.0% of the theoretical value.

Synthesis Example 2

20.43 g (0.1 mol) Irgacure 184 (CAS 947-19-3; 1-hydroxycyclohexyl phenyl ketone available from BASF SE) and 0.03 g tris(pentafluorobenze)borane were added into a 100 ml glass flask and heated to 30° C. 13.95 g (0.12 mol) of triethylsilane was added dropwise under stirring (60 minutes). The resulting mixture was stirred for another 10 minutes and then distilled under reduced pressure to obtain the desired siloxane modified photoinitiator. The obtained siloxane modified photoinitiator was a clear, light yellowish liquid.

The conversion yield of Irgacure 184 was 98.0% of the theoretical value.

Synthesis Example 3

34.04 g (0.1 mol) Irgacure 127 (CAS 474510-57-1; 2-hydroxy-1-(4-(4-(2-hydroxy-2-methylpropionyObenzyl)phenyl)-2-methylpropan-1-one available from BASF SE) and 0.127 g tris(pentafluorobenzene)borane were added into a 250 ml glass flask and heated to 50° C. 29.67 g (0.2 mol) of pentamethyldisiloxane was added dropwise under stirring (60 minutes). The resulting mixture was stirred for another 60 minutes. Thereafter 6.0 g basic aluminum oxide (Brockmann I, particle size ~150 mesh, available from Sigma-Aldrich) were added and the mixture was stirred for 15 minutes to absorb tris(pentafluorobenze)borane. Finally, the mixture was filtrated to obtain the desired siloxane modified photoinitiator. The obtained siloxane modified photoinitiator was a clear, light yellowish liquid.

Application Examples 1 and 2 and Comparative Examples 1 and 2

To test the performance of photoinitiators according to the invention (Application Examples 1 and 2), and commercial available photoinitiators (Comparative Examples 1 and 2), the photoinitiators outlined in table 1 below had been added to a UV curable organosilicone. The UV curable organosilicone polymer used was a methacrylic endcapped silanol terminated polydimethylsiloxane (polymer), which was prepared as described in Example 3 of U.S. Pat. No. 5,663,269. Each resulting mixture of photoinitiator and polymer was placed in between 2 layers of glass being 750 microns apart, and then subjected to UV irradiation using a Fusion System UV chamber with an H bulb for 30 seconds at 180 mW/cm$^2$ to cause curing.

After curing of the samples transmittance, haze and the b* value (yellowness) were measured by a Datacolor 650 apparatus available from Datacolor Corporation, in compliance with ASTM D1003 Standard Test Method. Thereafter the samples were subjected to reliability test conditions and the measurements were repeated.

Reliability test conditions: the cured samples were put in high temperature and high humidity chamber (85° C., 85% relative humidity) for 1000 hours.

The compositions of the mixtures tested, their appearance before curing, as well as the test results after curing and after having subjected the samples to reliability test conditions, i.e. after the aging test, are shown in Table 1.

TABLE 1

|  |  | Application example 1 | Application example 2 | Comparative example 1 | Comparative example 2 |
|---|---|---|---|---|---|
| Polymer [parts by weight] | | 99.2 | 99.2 | 99.2 | 99.2 |
| Photoinitiator [parts by weight] | | 0.8 Compound of synthesis example 1 | 0.8 Compound of synthesis example 2 | 0.8 Darocur 1173 | 0.8 Irgacure 184 |
| Appearance before curing | | Clear liquid | Clear liquid | Clear liquid* | Hazy liquid |
| Results after curing | Haze, % | 0.1 | 0.1 | 0.3 | — |
| | b* (yellowness) | 0.2 | 0.2 | 0.2 | |
| | Transmittance, % | >99% | >99% | >99% | |
| Results after aging test | Haze, % | 0.2 | 0.2 | 1.1 | — |
| | b* (yellowness) | 0.4 | 0.4 | 0.4 | |
| | Transmittance, % | >98% | >98% | >98% | |

*After 1 week's storage at ambient conditions, the clear liquid became hazy.

The results show that using photoinitiators according to the invention yields mixtures of lower haze than the comparative ones, indicating that photoinitiators according to the invention have improved compatibility with silicone material without sacrificing other important properties, in particular transmittance and non-yellowing.

What is claimed is:

1. A compound represented by the following formula (I):

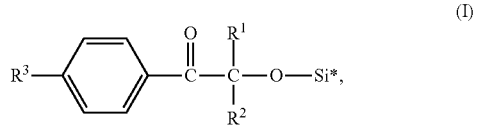

(I)

wherein
R¹ and R² each independently designates an alkyl group of 1 to 12 carbon atoms or a cycloalkyl group of 5 or 6 carbon atoms or R¹ and R² form together with the carbon atom to which they are attached a cycloaliphatic ring of 5 or 6 carbon atoms,
Si* represents an organopolysiloxane residue bonded via a silicon atom of this residue to the oxygen shown in formula (I), or a silane group SiR⁴R⁵R⁶, wherein R⁴, R⁵ and R⁶ each independently designates a cycloalkyl group of 5 or 6 carbon atoms or an aryl group of 6 to 10 carbon atoms, and
R³ designates a hydrogen atom or a group represented by the following formula (II)

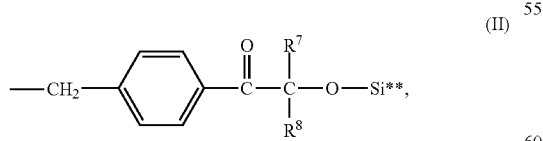

(II)

wherein
R⁷ and R⁸ each independently designates an alkyl group of 1 to 12 carbon atoms or a cycloalkyl group of 5 or 6 carbon atoms or R⁷ and R⁸ form together with the carbon atom to which they are attached a cycloaliphatic ring of 5 or 6 carbon atoms, and Si** represents an organopolysiloxane residue bonded via a silicon atom of this residue to the oxygen shown in formula (II), or a silane group SiR⁹R¹⁰R¹¹, wherein R⁹, R¹⁰ and R¹¹ each independently designates an alkyl group of 1 to 12 carbon atoms, a cycloalkyl group of 5 or 6 carbon atoms or an aryl group of 6 to 10 carbon atoms.

2. The compound according to claim 1, wherein R¹ and R² each independently designates methyl, ethyl, n-propyl or iso-propyl.

3. The compound according to claim 1, wherein R¹ and R² form together with the carbon atom to which they are attached a cyclohexyl ring.

4. The compound according to claim wherein R³ designates a hydrogen atom.

5. The compound according to claim 1, wherein R³ designates a group represented by formula (II), wherein R⁷ and R⁸ are identical to R¹ and R².

6. The compound according to claim 1, wherein R³ designates a group represented by formula (II), wherein Si** is identical to Si*.

7. The compound according to claim 1, wherein R¹ and R² each designates methyl and R³ designates a hydrogen atom.

8. The compound according to claim 1 wherein R¹ and R² form together with the carbon atom to which they are attached a cyclohexyl ring and R³ designates a hydrogen atom.

9. The compound according to claim 1, wherein R¹ and R² each designates methyl and R³ designates a group represented by formula (II), wherein R⁷ and R⁸ each designate methyl.

10. A method to produce a compound according to claim 1, reacting at least one α-hydroxy ketone of formula (I')

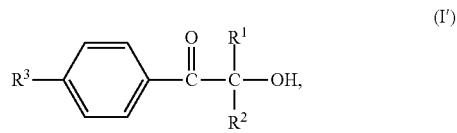

(I')

wherein
R¹ and R² each independently designates an alkyl group of 1 to 12 carbon atoms or a cycloalkyl group of 5 or 6 carbon atoms or R¹ and R² form together with the carbon atom to which they are attached a cycloaliphatic ring of 5 or 6 carbon atoms, and
R³ designates a hydrogen atom or a group represented by the following formula (II')

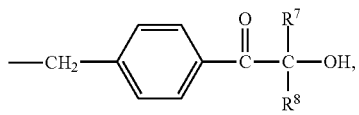

(II')

wherein
- $R^7$ and $R^8$ each independently designates an alkyl group of 1 to 12 carbon atoms or a cycloalkyl group of 5 or 6 carbon atoms or $R^7$ and $R^8$ form together with the carbon atom to which they are attached a cycloaliphatic ring of 5 or 6 carbon atoms,
- and at least one organopolysiloxane having at least one SiH group per molecule or at least one silane $HSiR^4R^5R^6$, wherein $R^4$, $R^5$ and $R^6$ each independently designates a cycloalkyl group of 5 or 6 carbon atoms or an aryl group of 6 to 10 carbon atoms, in the presence of a dehydrogenation catalyst.

11. The method according to claim 10, wherein the α-hydroxy ketone of formula (I') and the organopolysiloxane having at least one SiH group per molecule or the silane HSiR4R5R6 are reacted in respective amounts to provide a molar ratio of hydroxyl groups of the α-hydroxy ketone of formula (I') to SiH groups of 0.8 to 1.2.

12. A method according to claim 10, wherein the dehydrogenation catalyst is selected from tris(pentafluorobenzene)borane, zinc dust, and platinum catalysts.

13. A method according to claim 10, wherein the reaction is carried out at a temperature of from 20 to 100° C.

14. A method of using the compound according to claim 1 as photoinitiator and/or photosensitizer, comprising addition of the compound to a photopolymerizable organopolysiloxane or silicone resin and exposure of the resulting mixture to electromagnetic radiation.

15. The compound according to claim 1, wherein Si* represents a silane group $SiR^4R^5R6$, wherein $R^4$, $R^5$ and $R^6$ each independently an aryl group selected from phenyl and benzyl.

16. A compound represented by the following formula (I):

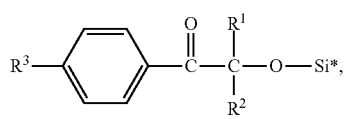

(I)

wherein
- $R^1$ and $R^2$ form together with the carbon atom to which they are attached a cyclohexyl ring;
- Si* represents an organopolysiloxane residue bonded via a silicon atom of this residue to the oxygen shown in formula (I), or a silane group $SiR^4R^5R^6$, wherein $R^4$, $R^5$ and $R^6$ each independently designates ethyl, n-propyl or isopropyl; and
- $R^3$ designates a hydrogen atom or a group represented by the following formula (II)

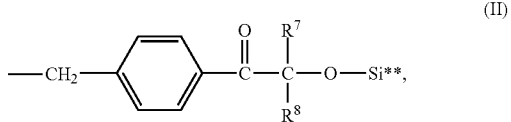

(II)

wherein
- $R^7$ and $R^8$ form together with the carbon atom to which they are attached a cyclohexyl ring; and
- Si** is identical to Si*.

17. The compound according to claim 16, wherein $R^3$ designates a hydrogen atom.

* * * * *